(12) United States Patent
Baek et al.

(10) Patent No.: US 11,109,790 B2
(45) Date of Patent: Sep. 7, 2021

(54) PATCH INCLUDING AN EXTERNAL FLOATING HIGH-PASS FILTER AND AN ELECTROCARDIOGRAPH (ECG) PATCH INCLUDING THE SAME

(71) Applicant: SAMSUNG ELECTRONICS CO., LTD., Suwon-si (KR)

(72) Inventors: Min Gun Baek, Seoul (KR); Long Yan, Hwaseong-si (KR); Hee Jae Jo, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 968 days.

(21) Appl. No.: 15/354,104

(22) Filed: Nov. 17, 2016

(65) Prior Publication Data

US 2017/0135595 A1     May 18, 2017

Related U.S. Application Data

(60) Provisional application No. 62/256,951, filed on Nov. 18, 2015.

(30) Foreign Application Priority Data

Mar. 9, 2016  (KR) .................. 10-2016-0028210

(51) Int. Cl.
*A61B 5/05*    (2021.01)
*A61B 5/04*    (2006.01)
(Continued)

(52) U.S. Cl.
CPC ............. *A61B 5/316* (2021.01); *A61B 5/259* (2021.01); *A61B 5/282* (2021.01); *A61B 5/301* (2021.01);
(Continued)

(58) Field of Classification Search
CPC . A61B 5/04085; A61B 5/0245; A61B 5/0006; A61B 5/0402; A61B 5/04012;
(Continued)

(56) References Cited

U.S. PATENT DOCUMENTS 6,249,696 B1 * 6/2001 Olson .................. A61B 5/0428
128/901
8,366,628 B2 2/2013 Denker et al.
(Continued)

FOREIGN PATENT DOCUMENTS

CN    101534706 A    9/2009
CN    103006256    4/2013
(Continued)

OTHER PUBLICATIONS

PCBWay "Multilayer PCB" Jan. 2014. (Year: 2014).*
(Continued)

*Primary Examiner* — Joseph A Stoklosa
*Assistant Examiner* — Brian M Antiskay
(74) *Attorney, Agent, or Firm* — F. Chau & Associates, LLC

(57) ABSTRACT

An electrocardiograph (ECG) patch including: a first electrode; a second electrode; a high pass filter configured to receive a bias voltage and provide the bias voltage to the first electrode and the second electrode; and a signal processing unit configured to generate the bias voltage and provide the bias voltage to the high pass filter.

20 Claims, 10 Drawing Sheets

(51) Int. Cl.
  *A61B 5/316* (2021.01)
  *A61B 5/00* (2006.01)
  *A61B 5/259* (2021.01)
  *A61B 5/282* (2021.01)
  *A61B 5/301* (2021.01)
  *A61B 5/30* (2021.01)

(52) U.S. Cl.
  CPC .......... *A61B 5/6823* (2013.01); *A61B 5/6832* (2013.01); *A61B 5/7203* (2013.01); *A61B 5/725* (2013.01); *A61B 5/30* (2021.01); *A61B 2560/0412* (2013.01); *A61B 2560/0468* (2013.01); *A61B 2562/222* (2013.01)

(58) Field of Classification Search
  CPC ... A61B 5/04017; A61B 5/024; A61B 5/7203; A61B 5/7225; A61B 2018/00351; A61N 1/3702; A61N 1/0484; H01L 2924/3025; H01L 29/78603
  USPC ......... 600/372, 382–384, 386–393, 508–509
  See application file for complete search history.

(56) References Cited

U.S. PATENT DOCUMENTS

| | | | |
|---|---|---|---|
| 8,390,374 B2* | 3/2013 | Alexander | H03F 3/45475 330/69 |
| 8,862,210 B2 | 10/2014 | Yazicioglu et al. | |
| 2003/0149349 A1* | 8/2003 | Jensen | A61B 5/02055 600/372 |
| 2006/0276715 A1* | 12/2006 | Yeo | A61B 5/0408 600/509 |
| 2007/0106170 A1* | 5/2007 | Dunseath, Jr. | A61B 5/0478 600/544 |
| 2008/0139953 A1* | 6/2008 | Baker | A61B 5/04085 600/509 |
| 2008/0150631 A1 | 6/2008 | Kim et al. | |
| 2011/0009729 A1 | 1/2011 | Shin et al. | |
| 2011/0092826 A1 | 4/2011 | Lee et al. | |
| 2011/0208028 A1* | 8/2011 | Rossi | A61B 5/053 600/372 |
| 2012/0089039 A1* | 4/2012 | Felix | A61B 5/7203 600/523 |
| 2014/0100432 A1* | 4/2014 | Golda | A61B 5/04325 600/301 |
| 2014/0221650 A1 | 8/2014 | Farringdon et al. | |
| 2014/0221850 A1 | 8/2014 | Farringdon et al. | |
| 2014/0228665 A1 | 8/2014 | Albert | |
| 2014/0285216 A1* | 9/2014 | Cuddihy | B60N 2/002 324/658 |
| 2015/0126844 A1 | 5/2015 | Yang et al. | |
| 2016/0007877 A1* | 1/2016 | Felix | A61B 5/0404 600/523 |
| 2016/0095527 A1* | 4/2016 | Thng | A61B 5/6808 600/301 |
| 2018/0242916 A1* | 8/2018 | Purdon | A61B 5/7203 |

FOREIGN PATENT DOCUMENTS

| | | |
|---|---|---|
| CN | 104812296 | 7/2015 |
| JP | 2001-198097 | 7/2001 |
| JP | 2007-082938 | 4/2007 |
| JP | 2011-224085 | 11/2011 |
| KR | 10-2012-0097997 | 9/2012 |
| KR | 1020120097997 | 9/2012 |
| KR | 10-1268498 | 6/2013 |
| KR | 10-1367208 | 10/2013 |
| KR | 1020140144009 | 12/2014 |
| KR | 1020150057388 | 5/2015 |

OTHER PUBLICATIONS

Electrosoft Engineering "Concepts and terminology used in Printed Circuit Boards (PCB)" 2010. (Year: 2010).*
European Search Report dated Apr. 7, 2017, Corresponding to European Patent Application No. 16199339.9.
Chinese Office Action issued in corresponding Chinese Patent Application No. 201611035440.6 dated Jun. 18, 2020.
Chinese Office Action issued in corresponding Chinese Patent Application No. 201611035440.6 dated Jan. 29, 2021.

* cited by examiner

PATCH INCLUDING AN EXTERNAL FLOATING HIGH-PASS FILTER AND AN ELECTROCARDIOGRAPH (ECG) PATCH INCLUDING THE SAME

CROSS-REFERENCE TO RELATED APPLICATIONS

This application claims priority under 35 U.S.C. § 119(e) to U.S. Provisional Patent Application No. 62/256,951 filed on Nov. 18, 2015, and under 35 U.S.C. § 119(a) to Korean Patent Application No. 10-2016-0028210 filed on Mar. 9, 2016, the disclosures of which are incorporated by reference herein in their entireties.

TECHNICAL FIELD

Exemplary embodiments of the inventive concept relate to an electrocardiograph (ECG) patch, and more particularly, to an ECG patch including two electrodes and a floating high-pass filter.

DISCUSSION OF RELATED ART

ECG monitoring is the process of recording the electrical activity of the heart over a period of time using electrodes placed on a person's body. These electrodes detect tiny electrical changes on the person's skin that arise from the heart depolarizing during each heartbeat. An ECG patch placed near the heart allows ECG signals to be easily acquired. Generally, an ECG patch includes ECG electrodes for detecting ECG signals and a bias electrode for supplying a bias voltage to a person's body. The bias electrode is typically attached to the person's body together with the ECG electrodes.

SUMMARY

According to an exemplary embodiment of the inventive concept, there is provided an electrocardiograph (ECG) patch comprising: a first electrode; a second electrode; a high pass filter configured to receive a bias voltage and provide the bias voltage to the first electrode and the second electrode; and a signal processing unit configured to generate the bias voltage and provide the bias voltage to the high pass filter.

The signal processing unit includes: a voltage regulator configured to receive an operating voltage; a voltage divider configured to divide the voltage that has been regulated by the voltage regulator to generate the bias voltage; and a driver configured to drive the bias voltage to the high pass filter.

The driver is a current driver.

The operating voltage is provided from a battery to the voltage regulator.

The high pass filter is a floating high pass filter.

According to an exemplary embodiment of the inventive concept, there is provided an ECG patch comprising: a first patch including a first electrode, a high pass filter and an ECG signal processing unit; a second patch including a second electrode and a battery; and a cable including a first wire for providing a bias voltage from the first patch to the second electrode, a second wire for providing an operating voltage to the second patch and a third wire for providing a ground voltage to the second patch.

The ECG signal processing unit comprises: a voltage regulator configured to receive the operating voltage; a voltage divider configured to divide the voltage that has been regulated by the voltage regulator to generate the bias voltage; and a driver configured to drive the bias voltage to the high pass filter.

The high pass filter is configured to receive the bias voltage from the ECG signal processing unit, provide the bias voltage to the first electrode and provide the bias voltage to the second electrode through the first wire.

The high pass filter is configured to perform a high pass filtering on a first ECG signal detected by the first electrode to generate a first high pass signal, and to perform a high pass filtering on a second ECG signal detected by the second electrode to generate a second high pass signal, and wherein the ECG signal processing unit is configured to generate an ECG output signal based on a difference between the first high pass filtered ECG signal and the second high pass filtered ECG signal.

The first patch includes a printed circuit board having a plurality of layers, and wherein the ECG signal processing unit is disposed at a first layer of the plurality of layers and the high pass filter is disposed at a last layer of the plurality of layers.

The ECG signal processing unit and the high pass filter are disposed opposite each other.

A transmission line for transmitting a ground voltage is configured to shield a transmission line for transmitting a first high pass filtered signal.

A shielding layer is disposed between the high pass filter and signal lines of the ECG signal processing unit.

According to an exemplary embodiment of the inventive concept, there is provided a data processing system comprising: an ECG patch comprising a first electrode, a second electrode, a high pass filter configured to generate a bias voltage to be provided to the first electrode and the second electrode, and a wireless transceiver; and a mobile communication device configured to communicate with the ECG patch.

The mobile communication device communicates with the ECG patch through a network.

The mobile communication device includes an app that displays data provided from the ECG patch, wherein the data provided from the ECG patch is medical data of a person wearing the ECG patch.

The mobile communication device provides a user with information based on the data provided from the ECG patch to medically assist the person wearing the ECG patch.

According to an exemplary embodiment of the inventive concept, there is provided a data processing system comprising: an ECG patch comprising a first electrode, a second electrode, a high pass filter configured to generate a bias voltage to be provided to the first electrode and the second electrode, and a wireless transceiver; a health care server configured to receive ECG medical data of a person wearing the ECG patch; and a mobile computing device configured to the receive the ECG medical data of the person from the health care server.

The mobile communication device presents a medical professional with the ECG medical data from the health care server to enable the medical professional to diagnose the person.

The ECG medical data of the patient is stored in the health care server.

The mobile communication device presents a medical professional with the ECG medical data from the health care server and medical history data of the person from the health care server to enable the medical professional to the diagnose the person.

The data processing system further comprises an internet of things (IoT) device configured to display data related to the diagnosis to the person.

The data processing system further comprises an IoT device configured to provide the ECG medical data from the ECG patch to the health care server.

According to an exemplary embodiment of the inventive concept, an ECG patch comprises: a first electrode configured to detect a first ECG signal; a second electrode configured to detect a second ECG signal; a high-pass filter configured to perform high-pass filtering on the first ECG signal to generate a first high-pass filtered signal, and to perform high-pass filtering on the second ECG signal to generate a second high-pass filtered signal; and a signal processing unit configured to generate an ECG output signal based on a difference between the first ECG signal and the second ECG signal, wherein the high-pass filter is further configured to generate a first bias voltage based on a driving voltage and provide the first bias voltage to the first electrode, and to generate a second bias voltage based on the driving voltage and provide the second bias voltage to the second electrode.

The first bias voltage and the second bias voltage have the same level.

The first ECG signal is detected when the first bias voltage is applied to a person's body and the second ECG signal is detected when the second bias voltage is applied to the person's body.

The high-pass filter is a floating high-pass filter.

The high-pass filter comprises: a first capacitor connected between a first transmission line and a third transmission line, wherein the first transmission line is connected to a first pad of the signal processing unit; a second capacitor connected between a first wire and a second transmission line, wherein the second capacitor is connected to a second pad of the signal processing unit; a first resistor connected between the third transmission line and a first node connected to a fifth pad of the signal processing unit; a second resistor connected between the first transmission line and the first node; a third resistor connected between the first node and the second transmission line; and a fourth resistor connected between the first node and the first wire.

The first and second capacitors have the same capacitances as each other and the first to fourth resistors have the same resistances as each other.

The signal processing unit comprises: a voltage regulator connected to a third pad of the signal processing unit and configured to receive an operating voltage via the third pad and regulate the operating voltage, wherein the third pad is connected to a second wire; a voltage divider configured to divide the voltage that has been regulated by the voltage generator to generate a driving voltage; and a driver configured to drive the driving voltage and provide the driving voltage to the high-pass filter through the fifth pad.

The first and second wires are included in a connector connecting the first and second electrodes to each other.

The ECG patch further comprises a battery configured to provide the operating voltage to the voltage regulator via the second wire.

The third transmission line is connected between the first electrode and the high-pass filter and the first wire is connected between the second electrode and the high-pass filter.

According to an exemplary embodiment of the inventive concept, an ECG patch comprises: a first patch including a first electrode and an ECG sensor; a second patch including a second electrode; and a cable connected between the first patch and the second patch, wherein the ECG sensor is configured to receive a first high-pass filtered signal and a second high-pass filtered signal and amplify a voltage difference between the first and second high-pass filtered signals to generate an output voltage, wherein the first patch includes a high-pass filter configured to generate a first bias voltage and a second bias voltage using a driving voltage and to provide the first bias voltage to the first electrode and the second bias voltage to the second electrode.

The first patch includes a printed circuit board (PCB) having a plurality of layers, wherein the ECG sensor is placed at a first side of the PCB and the high-pass filter is placed at a second side of the PCB, wherein the first and second sides are opposite each other.

A transmission line for transmitting the first high-pass filtered signal and the high-pass filter are placed at the same layer and a transmission line for transmitting a ground voltage is configured to shield the transmission line for transmitting the first high-pass filtered signal.

According to an exemplary embodiment of the inventive concept, there is provided an ECG patch comprising: a first electrode; a second electrode; a wire; and a high-pass filter configured to generate a first bias voltage and a second bias voltage, apply the first bias voltage to the first electrode via a transmission line and apply the second bias voltage to the second electrode via the wire.

The ECG further comprises: a signal processing unit configured to generate a driving voltage and provide the driving voltage to the high pass filter, wherein the high pass filter uses the driving voltage to generate the first and second bias voltages.

The driving voltage is based on an operating voltage provided through the wire.

The wire includes an operating voltage line and a bias voltage line.

According to an exemplary embodiment of the inventive concept, there is provided an ECG patch comprising: a first electrode configured to detect a first ECG signal from a heart of a person; a second electrode configured to detect a second ECG signal from the heart of the person; a high-pass filter configured to perform high-pass filtering on the first ECG signal to generate a first high-pass filtered signal, and to perform high-pass filtering on the second ECG signal to generate a second high-pass filtered signal; and an ECG processing unit including an ECG sensor configured to sense a difference between the first high-pass filtered signal and the second high-pass filtered signal and generate an ECG output signal corresponding to the sensing result, and a bias voltage generating circuit configured to provide a bias voltage to the high pass filter.

The ECG processing unit further comprises: an analog-to-digital converter configured to convert the ECG output signal into an ECG digital signal; a processing unit configured to analyze a heart rhythm of the person using the ECG digital signal; and a wireless transceiver configured to transmit data related to the heart rhythm of the person to an external device.

The external device includes an internet of things device.

The external device is configured to display the data related to the heart rhythm of the person.

The ECG processing unit further comprises a memory configured to store personal information and biological information of the person.

The personal information includes age, blood type, doctor's name, or medical history of the person, and the biological information includes a heart rate or an ECG waveform of the person.

The ECG processing unit further comprises a security circuit configured to encode the data related to the heart rhythm of the person.

The external device includes a health care sever.

BRIEF DESCRIPTION OF THE DRAWINGS

The above and other features of the inventive concept will become more apparent by describing in detail exemplary embodiments thereof with reference to the attached drawings in which.

DETAILED DESCRIPTION OF THE EMBODIMENTS

Figure 1:
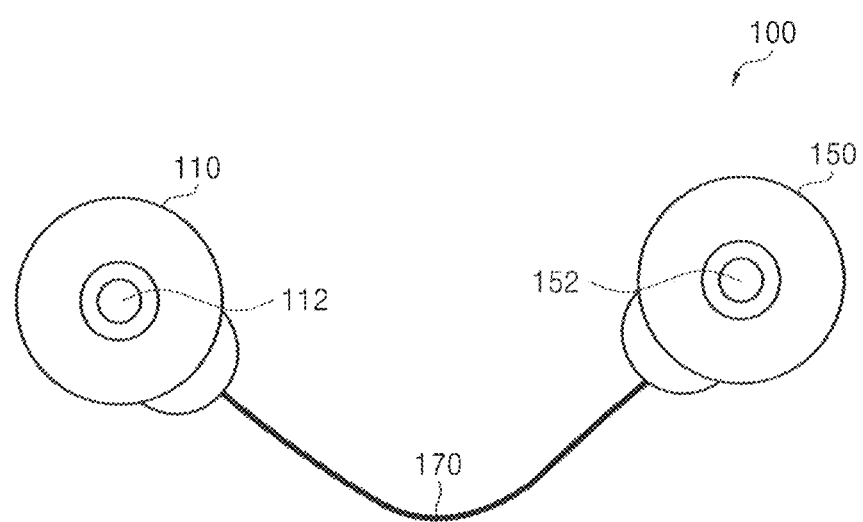
FIG. 1 is a perspective view of a wearable electrocardiograph (ECG) patch including two ECG electrodes and a floating high-pass filter according to an exemplary embodiment of the inventive concept.

Exemplary embodiments of the inventive concept will now be described more fully hereinafter with reference to the accompanying drawings. This inventive concept may, however, be embodied in many different forms and should not be construed as limited to the embodiments set forth herein. In the drawings, the size and relative sizes of layers and regions may be exaggerated for clarity. Like numbers refer to like elements throughout this application.

It will be understood that when an element is referred to as being "connected" or "coupled" to another element, it can be directly connected or coupled to the other element or intervening elements may be present.

As used herein, the singular forms "a", "an" and "the" are intended to include the plural forms as well, unless the context clearly indicates otherwise.

Figure 2:
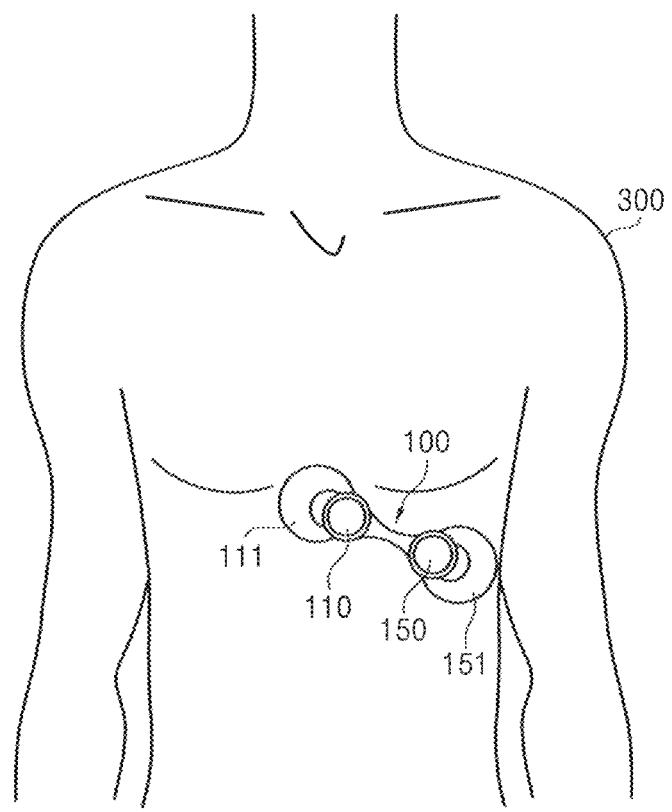
FIG. 2 is a perspective view showing a state where the wearable ECG patch illustrated in FIG. 1 is placed around a human heart, according to an exemplary embodiment of the inventive concept.

FIG. 1 is a perspective view of a wearable electrocardiograph (ECG) patch 100 including two ECG electrodes and a floating high-pass filter according to an exemplary embodiment of the inventive concept. FIG. 2 is a perspective view showing a state where the wearable ECG patch 100 illustrated in FIG. 1 is placed around a human heart, according to an exemplary embodiment of the inventive concept.

Referring to FIG. 1, the wearable ECG patch 100 may include a first patch 110, a second patch 150, and a cable 170. The wearable ECG patch 100 may be called an ECG patch or an ECG sensor patch.

ECG electrodes 112 and 152 are placed on the patches 110 and 150, respectively. The wearable ECG patch 100 does not require special ECG electrodes for body biasing to be implemented in any of the patches 110 and 150. Accordingly, the wearable ECG patch 100 includes only two ECG electrodes 112 and 152. The ECG electrodes 112 and 152 are ECG electrodes or ECG signal electrodes which are placed on the body, and more particularly, around the heart of a person 300.

In FIG. 2, reference numeral 111 denotes an adhesive layer for fixing or attaching the first ECG electrode 112 of the first patch 110 to the surface of the person's chest around the heart and reference numeral 151 denotes an adhesive layer for fixing or attaching the second ECG electrode 152 of the second patch 150 to the surface of the person's chest around the heart. Each of the adhesive layers 111 and 151 may include a conductive gel but is not limited thereto. In addition, reference numerals 111 and 151 may denote disposable ECG electrodes which are electrically connected to ECG electrodes 112 and 152, respectively.

Figure 3:
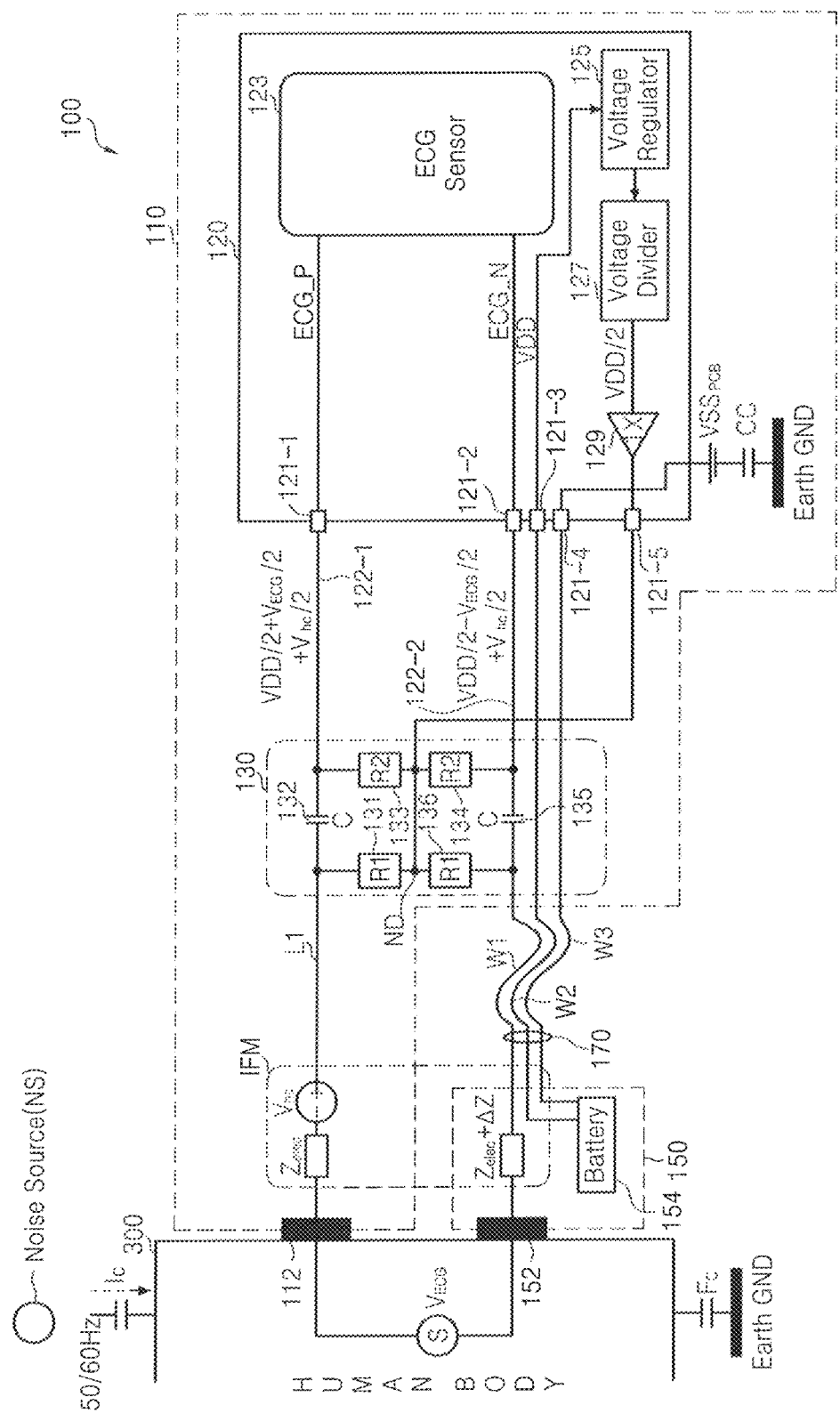
FIG. 3 is a detailed block diagram of the wearable ECG patch illustrated in FIG. 1, according to an exemplary embodiment of the inventive concept.

FIG. 3 is a detailed block diagram of the wearable ECG patch 100 illustrated in FIG. 1, according to an exemplary embodiment of the inventive concept. Referring to FIG. 3, $V_{ECG}$ denotes the voltage of an ECG signal generated by the heartbeat of the person 300; $Z_{elec}$ in an electrode interface model IFM denotes a contact impedance between each modeled ECG electrode 112 or 152 and the person 300; $V_{hc}$ denotes a voltage difference, e.g., a direct current (DC) component between the ECG electrodes 112 and 152; and $\Delta Z$ denotes a difference between the impedance of the first patch 110 and the contact impedance of the second patch 150. $\Delta Z$ is one of the factors increasing motion noise. The motion noise may be increased by the motion of the person 300 or a physical difference between the ECG electrodes 112 and 152 (e.g., a difference between the thicknesses of the adhesive layers 111 and 151 existing between the respective ECG electrodes 112 and 152 and the body of the person 300). The contact impedance $Z_{elec}$ may be determined by resistance (e.g., 51 kΩ) and capacitance (e.g., 47 nF) and the voltage difference $V_{hc}$ may be ±300 mV, but these values 51 kΩ, 47 nF, and ±300 mV are just examples.

50/60 Hz denotes power noise generated from a noise source (NS) and $I_C$ denotes noise current generated from the NS. For instance, when the person 300 with the wearable ECG patch 100 placed on the body around the heart is near the NS, e.g., a fluorescent light or a measuring device, which operates at a frequency of 50 or 60 Hz, the power noise 50/60 Hz and the noise current $I_C$ may influence the body of the person 300. $F_C$ denotes capacitance between an earth ground (GND) and the body of the person 300; $VSS_{PCB}$ denotes a ground (or a ground of a printed circuit board (PCB)) of an ECG signal processing unit 120; and CC denotes capacitance between the earth GND and the PCB ground $VSS_{PCB}$.

Referring to FIGS. 1 through 3, the first patch 110 includes the first ECG electrode 112, the ECG signal processing unit 120, a high-pass filter 130, and transmission lines 122-1, 122-2, and L1.

The first ECG electrode 112 may detect a first ECG signal from the heart of the person 300. The high-pass filter 130 may perform high-pass filtering on the first ECG signal to generate a first high-pass filtered ECG signal ECG_P.

The ECG signal processing unit 120 may include a plurality of pads 121-1, 121-2, 121-3, 121-4, and 121-5, an ECG sensor 123, a voltage regulator 125, a voltage divider 127, and a driver 129. The ECG signal processing unit 120, which can process bio signals ECG_P and ECG_N, may be an ECG chip or a bio-processor.

The ECG sensor 123 may sense a difference between the first high-pass filtered ECG signal ECG_P input through the first pad 121-1 and a second high-pass filtered ECG signal ECG_N input through the second pad 121-2 and may generate and process an ECG output signal corresponding to the sensing result.

The voltage regulator 125 may receive an operating voltage VDD through the third pad 121-3, may regulate the operating voltage VDD, and may generate an operating voltage of the ECG sensor 123 included in the ECG signal processing unit 120. The operating voltage VDD is generated by a battery 154 embedded in the second patch 150 and may be supplied to the voltage regulator 125 through a second wire W2 and the third pad 121-3.

The voltage divider 127 may divide the voltage (e.g., VDD) that has been regulated by the voltage regulator 125 to generate a driving voltage. The driving voltage may be VDD/2 but is not limited thereto. The driver 129 may drive the driving voltage VDD/2 to the high-pass filter 130 through the fifth pad 121-5. The driver 129 may have a gain of 1 and may be implemented as a current driver, but the inventive concept is not limited to this example.

The high-pass filter 130 may generate a first bias voltage and a second bias voltage using the driving voltage VDD/2, may apply the first bias voltage to the body of the person 300 through the third transmission line L1 and the first ECG electrode 112, and may apply the second bias voltage to the body of the person 300 through a first wire W1 and the second ECG electrode 152. The level of the first bias voltage may be the same as the level of the second bias voltage, but the inventive concept is not limited to this example. The levels of the first and second bias voltages may be determined by the driving voltage, e.g., VDD/2, output from the driver 129 when the ECG electrodes 112 and 152 are attached to the body of the person 300.

Accordingly, the first ECG electrode 112 may apply the first bias voltage to the body of the person 300 and detect a first ECG signal at a time, and the second ECG electrode 152 may apply the second bias voltage to the body of the person 300 and detect a second ECG signal at a time. The times may be the same, substantially simultaneous or different from each other.

Since the driving voltage VDD/2 is applied to the high-pass filter 130, the high-pass filter 130 may be implemented as a floating high-pass filter. The high-pass filter 130 may include a plurality of capacitors 132 and 135 and a plurality of resistors 131, 133, 134, and 136. Although the high-pass filter 130 is placed outside the ECG signal processing unit 120 in the embodiment illustrated in FIG. 3, the high-pass filter 130 may be integrated into or placed within the ECG signal processing unit 120.

The first capacitor 132 is connected between the third transmission line L1 and the first transmission line 122-1. The second capacitor 135 is connected between the first wire W1 and the second transmission line 122-2. The first transmission line 122-1 is connected to the first pad 121-1. The second transmission line 122-2 is connected to the second pad 121-2.

The first resistor 131 is connected between the third transmission line L1 and a node ND connected to the fifth pad 121-5. The second resistor 133 is connected between the first transmission line 122-1 and the node ND. The third resistor 134 is connected between the node ND and the second transmission line 122-2. The fourth resistor 136 is connected between the node ND and the first wire W1.

The capacitors 132 and 135 may have the same capacitance C and the resistors 131, 133, 134, and 136 may have the same resistance R. However, the resistors 131 and 136 may have a resistance R1 and the resistors 133 and 134 may have a resistance R2. In this case, the resistance R1 may be different from the resistance R2. Each of the resistors 131, 133, 134, and 136 may be a passive or an active resistance element. Each of the capacitors 132 and 135 may be a switched capacitor.

A common-mode DC gain $G_{CM,\ DC}$ of the high-pass filter 130 may be 1. For instance, when R=R1=R2, a cutoff frequency $f_{HPf,\ -3dB}$ of the high-pass filter 130 is $1/2\pi$ RC and a differential input impedance $Z_{in,\ Diff}$ approximates R.

When the ECG electrodes 112 and 152 are attached to the body of the person 300 around the heart and the driving voltage VDD/2 is applied to the high-pass filter 130, a voltage of the first transmission line 122-1 is VDD/2+ $G1 \cdot V_{ECG}/2 + V_{hc}/2$ and a voltage of the second transmission line 122-2 is $VDD/2 - G1 \cdot V_{ECG}/2 + V_{hc}/2$, where G1 may denote a gain which is determined by the capacitance C, the resistance R2, and a frequency of the voltage $V_{ECG}$. Although the formulas illustrated in FIG. 3 do not include G1, in practice these formulas may include G1.

Accordingly, differential DC inputs (e.g., $V_{hc}$) are attenuated by the high-pass filter 130 and the attenuated differential DC inputs may be eliminated from the ECG sensor 123. The body of the person 300 is biased by two resistors 131 and 136 and two ECG electrodes 112 and 152. In other words, the ECG patch 100 does not include a separate bias electrode for exclusively supplying a bias voltage.

The ground of the battery 154 and the PCB ground $VSS_{PCB}$ may be connected with each other through a third wire W3 and the fourth pad 121-4.

The second patch 150 may include the second electrode 152 and the battery 154. The second ECG signal detected by the second electrode 152 is transmitted to the high-pass filter 130 through the first wire W1. The high-pass filter 130 performs high-pass filtering on the second ECG signal to output the second high-pass filtered ECG signal ECG_N. The second high-pass filtered ECG signal ECG_N may be transmitted to the ECG sensor 123 through the second transmission line 122-2 and the second pad 121-2.

The cable 170 may include the first wire W1 for transmitting the second ECG signal detected by the second ECG electrode 152 placed in the second patch 150 to the first patch 110, the second wire W2 for transmitting the operating voltage VDD to the first patch 110, and the third wire W3 for transmitting a ground voltage to the first patch 110. The cable 170 may be a shielded cable.

Figure 4:
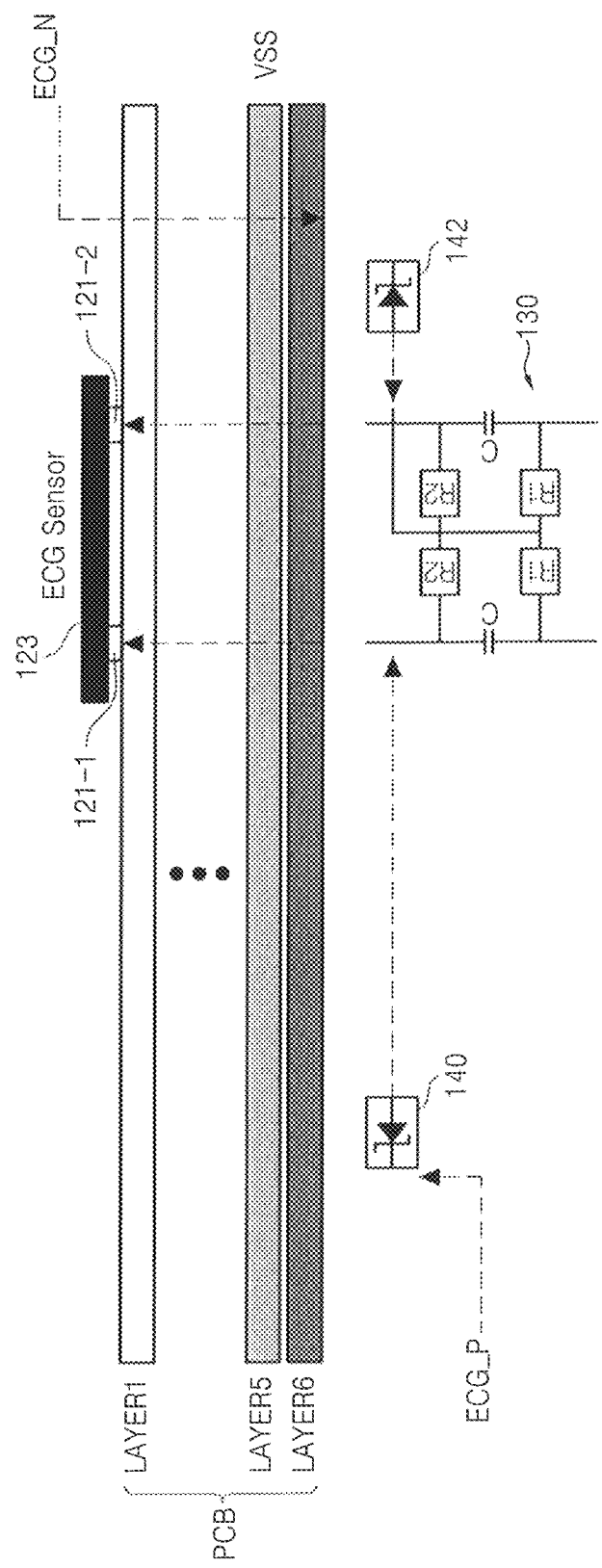
FIG. 4 is a schematic diagram of the layout of a floating high-pass filter and ECG transmission lines included in a first patch of the wearable ECG patch illustrated in FIG. 1, according to an exemplary embodiment of the inventive concept.

FIG. 4 is a schematic diagram of the layout of the floating high-pass filter 130 and ECG transmission lines included in the first patch 110 of the wearable ECG patch 100 illustrated in FIG. 1, according to an exemplary embodiment of the inventive concept. Referring to FIG. 4, when the ECG patch 100 is implemented in a PCB including a plurality of layers LAYER1 through LAYER6, the ECG signal processing unit 120 may be placed at the first layer LAYER1 and the high-pass filter 130 may be placed at the sixth layer LAYER6, but the inventive concept is not limited to the current embodiment.

A first electrostatic discharge (ESD) protection circuit 140 may be placed between the electrodes 112 and 152 and the high-pass filter 130. The high-pass filter 130 may be placed as close as possible to the ECG sensor 123. A transmission line for supplying a ground voltage VSS may be placed at the fifth layer LAYER5. ESD protection circuits 140 and 142, the first transmission line 122-1 for transmitting the first high-pass filtered ECG signal ECG_P, and the second transmission line 122-2 for transmitting the second high-pass filtered ECG signal ECG_N may be placed at the sixth layer LAYER6, but the inventive concept is not limited to the current embodiment.

Figure 5:
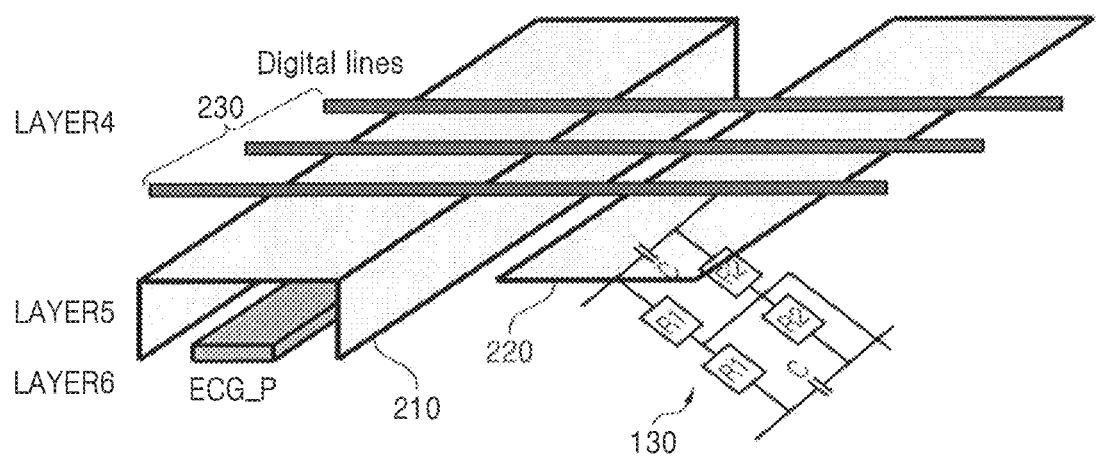
FIG. 5 is a schematic diagram of the layout of a printed circuit board (PCB) included in the first patch of the wearable ECG patch illustrated in FIG. 1, according to an exemplary embodiment of the inventive concept.

FIG. 5 is a schematic diagram of the layout of a PCB included in the first patch 110 of the wearable ECG patch 100 illustrated in FIG. 1, according to an exemplary embodiment of the inventive concept. Referring to FIG. 5, a transmission line for transmitting the first high-pass filtered ECG signal ECG_P and the high-pass filter 130 are placed at the sixth layer LAYER6, a transmission line 210 placed at the fifth layer LAYER5 to transmit a ground voltage may have a structure for shielding the transmission line for transmitting the first high-pass filtered ECG signal ECG_P to prevent coupling noise between digital lines 230 placed at the fourth layer LAYER4 and the transmission line placed at the sixth layer LAYER6 to transmit the first high-pass filtered ECG signal ECG_P. In addition, a shielding structure 220 or a shielding layer 220 may be placed between the digital lines 230 and the high-pass filter 130 to prevent coupling noise between the digital lines 230 and the high-pass filter 130.

Figure 6:
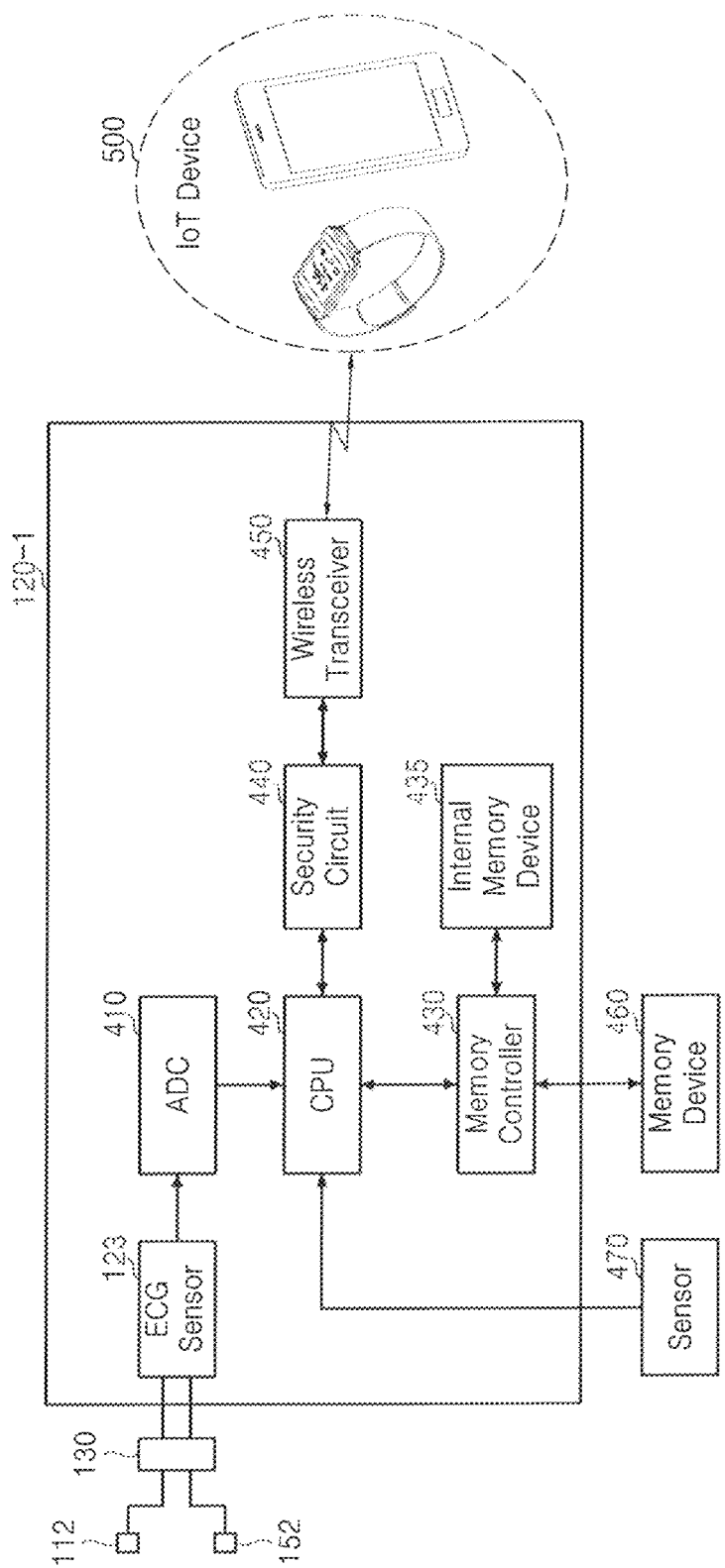
FIG. 6 is a detailed block diagram of the wearable ECG patch illustrated in FIG. 1, according to an exemplary embodiment of the inventive concept.

FIG. 6 is a detailed block diagram of the wearable ECG patch illustrated in FIG. 1, according to an exemplary embodiment of the inventive concept. Referring to FIGS. 1, 2, 3, and 6, an ECG processing unit 120-1 may include an ECG sensor 123, an analog-to-digital converter (ADC) 410, a central processing unit (CPU) 420, a memory controller 430, an internal memory device 435, a security circuit 440, and a wireless transceiver 450. Referring to FIGS. 1, 3, and 6, the ECG patch may include a memory device 460 and a sensor 470.

Referring to FIGS. 3 and 6, the ECG sensor 123 may receive a first high-pass filtered ECG signal ECG_P and a second high-pass filtered ECG signal ECG_N, process (or amplify) a voltage difference between the first high-pass filtered ECG signal ECG_P and the second high-pass filtered ECG signal ECG_N, and generate an ECG output corresponding to a result of the process (or amplification).

The ADC 410 may convert the ECG output into an ECG digital signal and output the ECG digital signal to the CPU 420. The CPU 420 may analyze a heart rhythm of a person using the ECG digital signal. The CPU 420 may detect, predict, or analyze sudden cardiac arrest (SCA) of a person using the ECG digital signal. For example, the CPU 420 may detect, predict, or analyze cardiac arrhythmias such as ventricular fibrillation and/or ventricular tachycardia using the ECG digital signal.

The memory controller 430, under the control of the CPU 420, may transmit data related to the high-pass filtered ECG signals ECG_P and ECG_N to the internal memory device 435 and/or the memory device 460 and receive data related to the high-pass filtered ECG signals ECG_P and ECG_N from the internal memory device 435 and/or the memory device 460.

The internal memory device 435 may be a read only memory (ROM), a random access memory (RAM), a dynamic RAM (DRAM), or a static RAM (SRAM), but is not limited thereto. The memory device 460 may store a boot image for booting the ECG patch 100 and an application program to be performed by the CPU 420. The memory device 460 may comprise a volatile memory and/or a non-volatile memory. The volatile memory may be a RAM, a DRAM, or an SRAM, but is not limited thereto. The non-volatile memory may be an electrically erasable programmable ROM (EEPROM), a NAND-type flash memory, a NOR-type flash memory, a magnetic RAM (MRAM), a spin-transfer torque MRAM, a ferroelectric RAM (FeRAM), a phase change RAM (PRAM), a resistive RAM (RRAM), a holographic memory, a molecular electronics memory device, or an insulator resistance change memory, but is not limited thereto.

The internal memory device 435 and/or the memory device 460 may store information on a person such as a patient (e.g., patient data) and/or data related to the high-pass filtered ECG signals ECG_P and ECG_N under the control of the memory controller 430. For example, the data may include high-pass filtered ECG signals ECG_P and ECG_N, data related to a heart rate, data related to cardiac arrhythmias, data related to ventricular fibrillation (e.g., a history of ventricular fibrillation and a history of defibrillation), and/or sensing data generated by the sensor 470. For example, the data may be encoded or decoded by the security circuit 440.

The security circuit 440 may encode data output from the CPU 420 and related to a heart rhythm into security data, and output the encoded security data to the wireless transceiver 450. In addition, the security circuit 440 may decode the data transmitted from the wireless transceiver 450 and transmit the decoded data to the CPU 420. For example, the security circuit 440 may be configured, e.g., programmed, with an encryption and decryption code.

The wireless transceiver 450 may transmit encoded security data output from the security circuit 440 to an external Internet of Things (IoT) device 500 (e.g., a wireless communication device, a smart watch, a smart phone, a tablet personal computer (PC), a wearable computer, a mobile internet device, etc.) under the control of the CPU 440. The ECG processing unit 120-1 may use a communication circuit, e.g., the wireless transceiver 450, for connecting to the external IoT device 500. For example, the ECG processing unit 120-1 may determine what kind of external smart device the communication circuit is connected to.

The wireless transceiver 450 may transmit data related to the high-pass filtered ECG signals ECG_P and ECG_N, e.g., security data or biological data, to the external IoT device 500 through a local area network (LAN), a wireless LAN (WLAN) such as wireless fidelity (Wi-Fi), a wireless personal area network (WPAN) such as Bluetooth, a wireless universal serial bus (USB), a Zigbee connection, a near field communication (NFC) connection, a radio-frequency identification (RFID) connection, or a mobile cellular network. For example, the mobile communication network may be a $3^{rd}$ generation (3G) mobile communication network, a $4^{th}$ generation (4G) mobile communication network, or a long term evolution mobile communication network (LTE™). For example, the wireless transceiver 450 may include a transceiver and an antenna for modem communication. The Bluetooth interface may support Bluetooth Low Energy (BLE).

Figure 7:
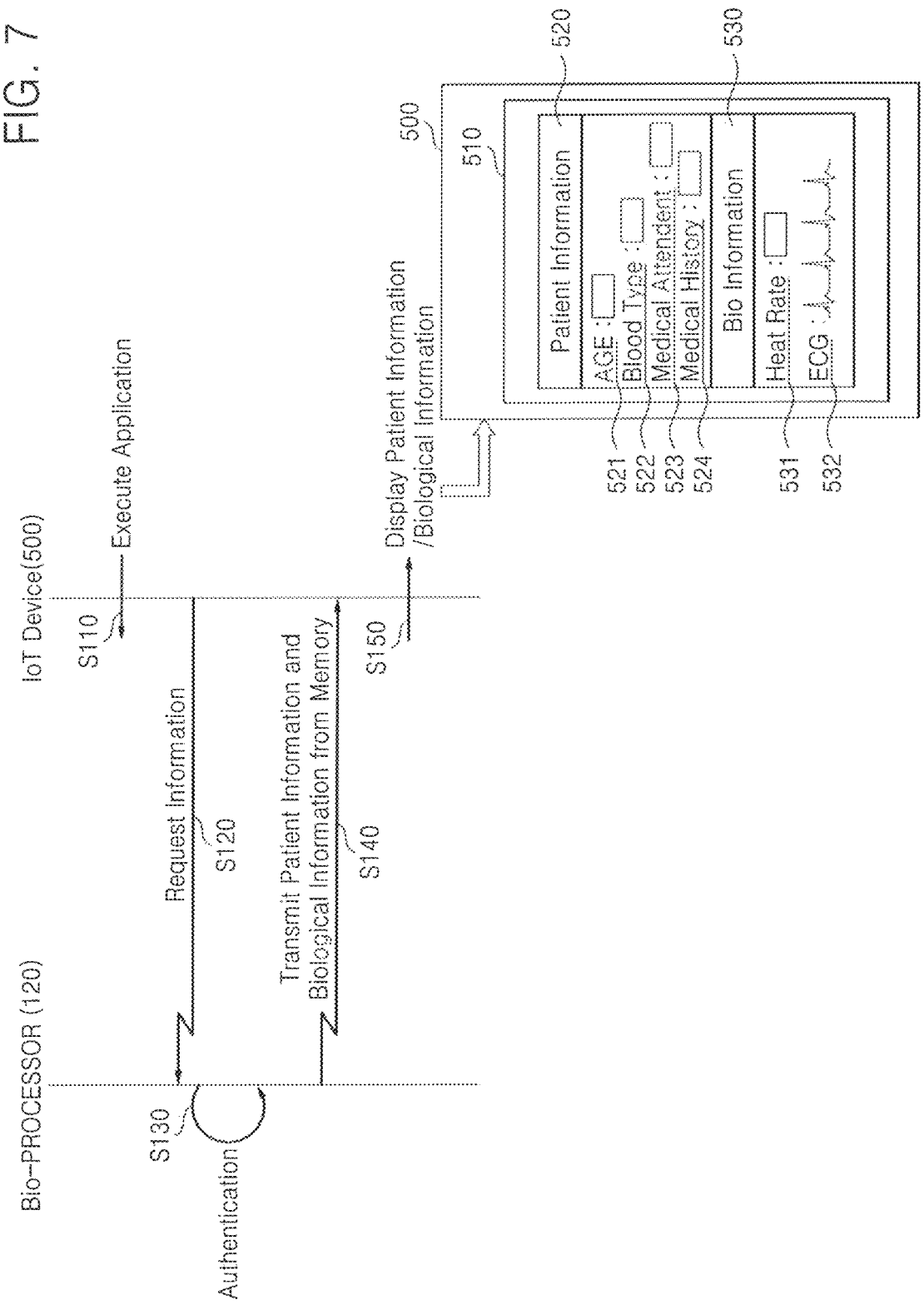
FIG. 7 is a diagram of a data processing system which includes the ECG signal processing unit shown in FIG. 6, according to an exemplary embodiment of the inventive concept.

FIG. 7 is a diagram of a data processing system which includes the ECG signal processing unit 120-1 shown in FIG. 6, according to an exemplary embodiment of the inventive concept. Referring to FIGS. 6 and 7, a user of a IoT device 500 may execute, e.g., select for use, an application installed in the IoT device 500 (S110).

A communication module (or wireless transceiver) of the IoT device 500 may transmit an information request to the ECG processing unit 120 or 120-1 (hereinafter collectively referred to as 120) under the control of the application performed by a CPU of the IoT device 500 (S120). A CPU 420 of the ECG processing unit 120, for example bio-processor 120, may require authentication by performing an information request through the wireless transceiver 450 (S130).

After the authentication is completed, the CPU 420 may read patient information and biological information from the memory device 435 or 460 using the memory controller 430, and transmit the patient information and the biological information to the wireless transceiver 450 through the security circuit 440. The wireless transceiver 450 may transmit the patient information and the biological information to the IoT device 500 through a wireless network (S140).

The application executed by a CPU included in the IoT device 500 may display patient information 520 and/or biological information 530 on a display device 510 of the IoT device 500 (S150). For example, the patient information 520 may include the age 521, blood type 522, family doctor (medical attendant) 523, and/or a medical history 524 of the patient. The biological information 530 may include heart rate 531 and an ECG waveform 532.

A user of the IoT device 500 may determine a state of a patient to which the wearable ECG patch 100 is attached using the patient information 520 and/or the biological information 530, and perform a proper medical treatment or emergency diagnosis on the patient according to a result of the determination.

Figure 8:
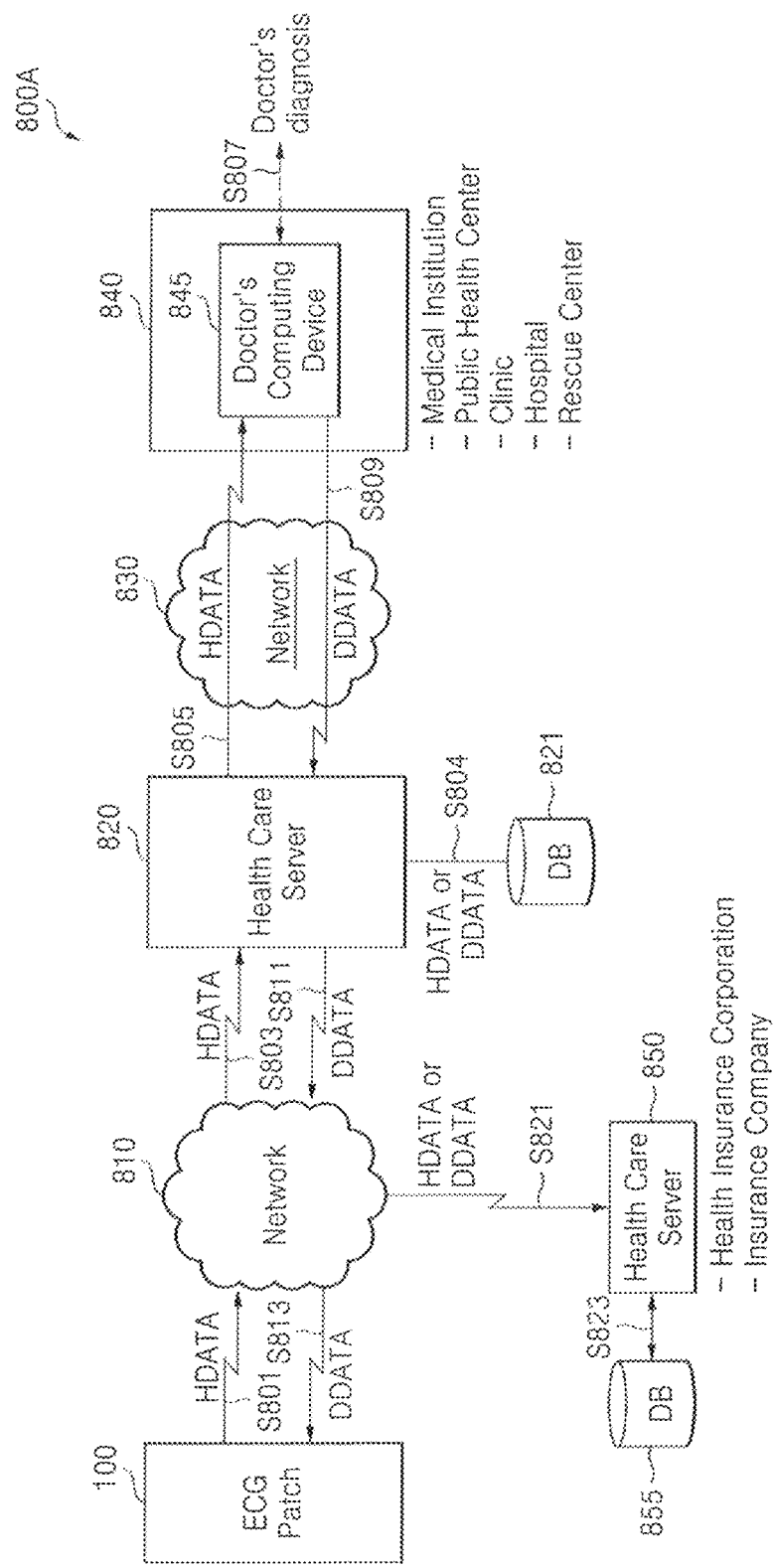
FIGS. 8, 9, and 10 are diagrams illustrating data processing systems which include the wearable ECG patch shown in FIG. 1, according to an exemplary embodiment of the inventive concept.
Figure 9:
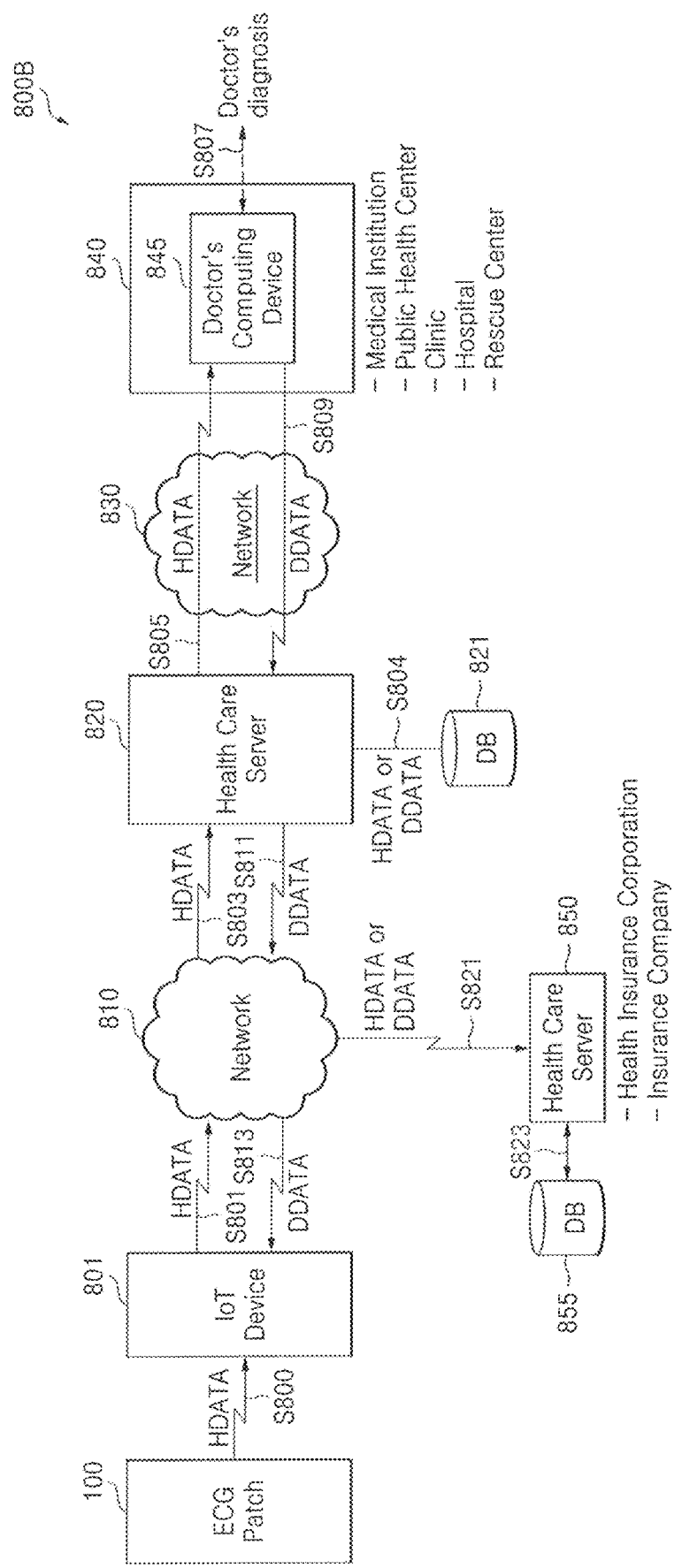
Figure 10:
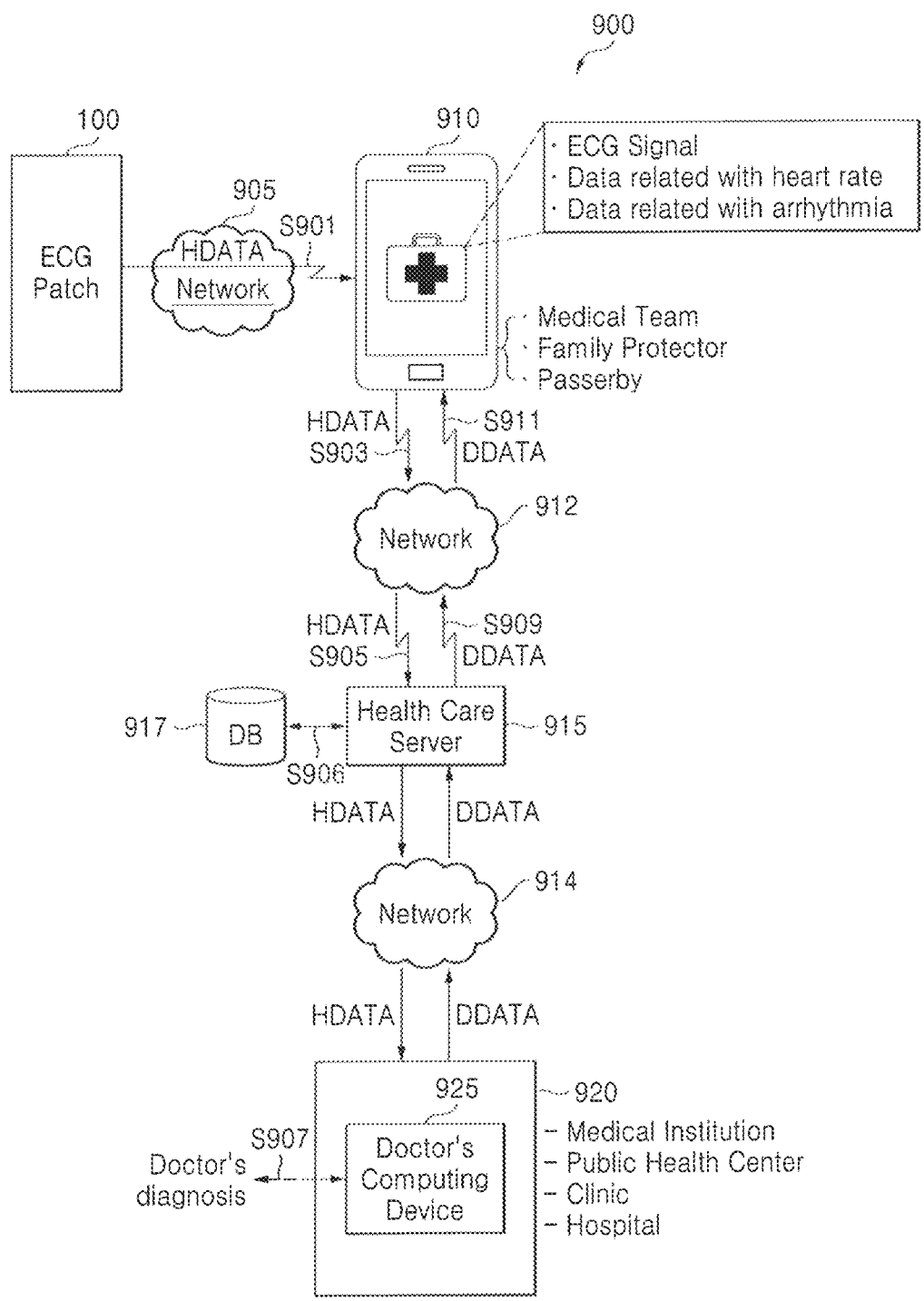

FIGS. 8, 9, and 10 are diagrams illustrating data processing systems which include the wearable ECG patch shown in FIG. 1, according to exemplary embodiments of the inventive concept. Referring to FIG. 8, a data processing system 800A may be used to provide a telemedicine service. The data processing system 800A may include the wearable ECG patch 100 and a first medical server (health care sever) 820 which can communicate with the wearable ECG patch 100 through a wireless network 810, e.g., the internet or Wi-Fi.

According to one example, the data processing system 800A may further include a second medical server (health care server) 850 which can communicate with the wearable ECG patch 100 and/or the first medical server 820 through the wireless network 810. For example, a health insurance corporation and/or an insurance company may manage the second medical server 850 and a database 855.

The wireless transceiver 450 of the wearable ECG patch 100 may transmit data HDATA corresponding to the ECG signals ECG_P and ECG_N. The application may store a uniform resource locator (URL) of the first medical server 820 and/or a URL of the second medical server 850. Accordingly, the wireless transceiver 450 of the wearable ECG patch 100 may transmit data HDATA to the first medical server 820 (S801) and/or the second medical server 850 (S821) through the network 810 under the control of the CPU 420 or a control of an application program ("app") performed by the CPU 420.

The data HDATA may include the ECG signals ECG_P and ECG_N, data generated based on the ECG signals ECG_P and ECG_N, and patient information. For example, data generated based on the ECG signals ECG_P and ECG_N may include data on ventricular fibrillation, data on ventricular tachycardia, a heart rate, arrhythmia, or a defibrillation history of the patient, but is not limited thereto.

The wireless network 810 may transmit the data HDATA to the first medical server 820 and/or the second medical server 850 (S803 and/or S821). The first medical server 820 may store the data HDATA in database 821 (S804), and transmit the data HDATA to a computing device 845 of a doctor working at a medical institution 840 through a network 830 (S805). For example, the computing device 845 of a doctor may be a PC or a tablet PC, but is not limited thereto. The doctor may work at a medical institution, a public health care center, a clinic, a hospital, or a rescue center, for example.

The doctor may diagnose a state of the patient using the data HDATA displayed through the computing device 845 and input diagnostic data into the computing device 845 (S807). The computing device 845 transmits the diagnostic data DDATA to the first medical server 820 through the network 830 (S809), and the first medical server 820 stores the diagnostic data DDATA in the database 821 (S804) and transmits the diagnostic data DDATA to the network 810 (S811). The network 810 may transmit the diagnostic data DDATA to the wearable ECG patch 100 (S813) or to the second medical server 850 (S821). The ECG patch 100 may store the diagnostic data DDATA in the memory device 435 or 460. The second medical server 850 may store the diagnostic data DDATA in the database 855 (S823).

Each of the servers 820 and 850 may store or analyze each of the data HDATA and DDATA in the databases 821 and 855. In addition, each of the servers 820 and 850 may transmit a result of the analysis to the networks 810 and 830.

Referring to FIG. 9, a data processing system 800B may be used to provide a remote medical service. The data processing system 800B may include the wearable ECG patch 100, an IoT device 801 (for example a smart watch or a smart phone), and the first medical server 820 which can communicate with the IoT device 801 through the wireless network 810. The IoT device 801 may be the IoT device 500 of the examples shown in and described with reference to FIGS. 6 and 7, but is not limited thereto. The data processing system 800A of FIG. 9 is similar to the data processing system 800B of FIG. 8, in terms of its structure and operation, except for the IoT device 801 through which the wearable ECG patch 100 transmits or receives data to or from the wireless network 810.

The wearable ECG patch 100 may transmit data HDATA generated by the wearable ECG patch 100 to the IoT device 801 (S800). For example, the wearable ECG patch 100 may automatically transmit the data HDATA to the IoT device 801 according to a request of the IoT device 801 or when an abnormality is detected in the heart function of a patient (S800). The IoT device 801 may transmit the data HDATA to the network 810 (S801), and receive diagnostic data DDATA output from the network 810 (S813). The IoT device 801 may display the diagnostic data DDATA on a display of the IoT device 801. Accordingly, a user of the IoT device 801 may provide appropriate medical care to or perform first aid on a patient who wears the wearable ECG patch 100, using the diagnostic data DDATA.

Referring to FIG. 10, a data processing system 900 may be used to provide a remote medical service. The data processing system 900 may include the wearable ECG patch 100 and a mobile computing device 910 which can communicate with the wearable ECG patch 100 through a network 905. The data processing system 900 may further include a medical server (health care server) 915 which can communicate with the mobile computing device 910 through a network 912.

The wireless transceiver 450 of the wearable ECG patch 100 may transmit data HDATA corresponding to the ECG signals ECG_P and ECG_N to the mobile computing device 910 through the network 905 under the control of the CPU 420 or a control of an app performed by the CPU 420 (S901).

For example, the mobile computing device 910 may be a smart phone, a tablet PC, a minimally invasive device (MID), an IoT device, or an internet of everything (IoE) device, but is not limited thereto. A user of the mobile computing device 910 which can perform an app to be described with reference to FIG. 10 may be a medical team, a guardian, or a passerby. The passerby may be someone who has completed first aid training; however, the inventive concept is not limited thereto.

An app performed by a CPU of the mobile computing device 910 may be represented by an icon(s), interface, etc. displayed on a display of the mobile computing device 910. The mobile computing device 910 may transmit the data HDATA to the medical server 915 through the network 912 under the control of the app (S903 and S905). The mobile computing device 910 stores a URL of the medial server 915, such that the mobile computing device 910 may transmit the data HDATA to the medical server 915 corresponding to a URL under the control of an app (S903 and S905).

The medical server 915 may store the data HDATA in the database 917 (S906), and transmit the data HDATA to a computing device 925 of a doctor working at a medical institution 920 through a network 914.

The doctor may diagnose a state of a patient using the data HDATA displayed through the computing device 925 and input diagnostic data into the computing device 925 (S907). The computing device 925 may transmit the diagnostic data DDATA to the medical server 915 through the network 914, and the medical server 915 may store the diagnostic data DDATA in the database 917 (S906), and transmit the diagnostic data DDATA to the mobile computing device 910 through the network 912 (S909 and S911). The mobile computing device 910 may display the diagnostic data DDATA of the doctor on a display of the mobile computing device 910. Accordingly, a user of the mobile computing device 910 may provide appropriate medical care to or perform first aid on a patient who wears the wearable ECG patch 100, using the diagnostic data DDATA.

As described above, according to an exemplary embodiment of the inventive concept, an ECG patch includes two electrodes and a floating high-pass filter but does not include a bias electrode for applying a bias voltage to a human body. To generate the bias voltage, the ECG patch uses the high-pass filter, and applies the bias voltage to the human body through the ECG electrodes. In other words, since the ECG patch does not include a bias electrode, a form factor for the ECG patch is reduced in size. Further, since the ECG patch has a minimum number of electrodes, a contact area between the ECG patch and the skin is minimized, so that the convenience of attaching/detaching the ECG patch to the skin increases and an area of the skin impacted by the attached electrodes is also minimized.

While the inventive concept has been particularly shown and described with reference to exemplary embodiments thereof, it will be understood by those of ordinary skill in the art that various changes in forms and details may be made therein without departing from the spirit and scope of the inventive concept as defined by the following claims.

What is claimed is:

1. An electrocardiograph (ECG) patch, comprising:
 a first electrode;
 a second electrode;
 a high pass filter configured to receive a bias voltage and provide the bias voltage to the first electrode and the second electrode; and
 a signal processing unit configured to generate the bias voltage and provide the bias voltage to the high pass filter through a line connected between the high pass filter and the signal processing unit, wherein the line is connected to a first node of the high pass filter, the first node directly connected between a first resistor and a second resistor included in the high pass filter, the first resistor connected to a transmission line for providing the bias voltage to the first electrode, the second resistor connected to a wire for providing the bias voltage to the second electrode.

2. The ECG patch of claim 1, wherein the signal processing unit comprises:
 a voltage regulator configured to receive an operating voltage;
 a voltage divider configured to divide a voltage that has been regulated by the voltage regulator to generate the bias voltage; and
 a driver configured to drive the bias voltage to the high pass filter.

3. The ECG patch of claim 2, wherein the driver is a current driver.

4. The ECG patch of claim 2, wherein the operating voltage is provided from a battery to the voltage regulator.

5. The ECG patch of claim 1, wherein the high pass filter is a floating high pass filter.

6. An electrocardiograph (ECG) patch, comprising:
 a first patch including a first electrode, a high pass filter and an ECG signal processing unit, wherein the ECG signal processing unit generates and provides a bias voltage to the high pass filter;
 a second patch including a second electrode and a battery; and
 a cable including a first wire for providing the bias voltage from the first patch to the second electrode, a second wire for providing an operating voltage to the second patch and a third wire for providing a ground voltage to the second patch, wherein the first wire is directly connected to a pair of resistors included in the high pass filter, at least one of the pair of resistors being directly connected to a node that receives the bias voltage from the ECG signal processing unit.

7. The ECG patch of claim 6, wherein the ECG signal processing unit comprises:
 a voltage regulator configured to receive the operating voltage;
 a voltage divider configured to divide a voltage that has been regulated by the voltage regulator to generate the bias voltage; and
 a driver configured to drive the bias voltage to the high pass filter.

8. The ECG patch of claim 6, wherein the high pass filter is configured to receive the bias voltage from the ECG signal processing unit, provide the bias voltage to the first electrode and provide the bias voltage to the second electrode through the first wire.

9. The ECG patch of claim 6, wherein the high pass filter is configured to perform a high pass filtering on a first ECG signal detected by the first electrode to generate a first high pass, signal, and to perform a high pass filtering on a second ECG signal detected by the second electrode to generate a second high pass signal, and wherein the ECG signal processing unit is configured to generate an ECG output signal based on a difference between the first high pass filtered ECG signal and the second high pass filtered ECG signal.

10. The ECG patch of claim 6, wherein the first patch includes a printed circuit board having a plurality of layers, and wherein the ECG signal processing unit is disposed at a first layer of the plurality of layers and the high pass filter is disposed at a last layer of the plurality of layers.

11. The ECG patch of claim 10, wherein the ECG signal processing unit and the high pass filter are disposed opposite each other.

12. The ECG patch of claim 10, wherein a transmission line for transmitting a ground voltage is configured to shield a transmission line for transmitting a first high pass filtered signal.

13. The ECG patch of claim 12, wherein a shielding layer is disposed between the high pass filter and signal lines of the ECG signal processing unit.

14. An electrocardiograph (ECG) patch, comprising:
a first electrode configured to detect a first ECG signal;
a second electrode configured to detect a second ECG signal;
a high-pass filter configured to perform high-pass filtering on the first ECG signal to generate a first high-pass filtered signal, and to perform high-pass filtering on the second ECG signal to generate a second high-pass filtered signal; and
a signal processing unit configured to generate an ECG output signal based on a difference between the first ECG signal and the second ECG signal,
wherein the high-pass filter is further configured to generate a first bias voltage based on a driving voltage received from the signal processing unit and provide the first bias voltage to the first electrode, and to generate a second bias voltage based on the driving voltage and provide the second bias voltage to the second electrode,
wherein the signal processing unit is connected to a first node of the high-pass filter, the first node electrically connected to a first transmission line for providing the first bias voltage to the first electrode and a first wire for providing the second bias voltage to the second electrode, wherein the high-pass filter comprises: a first resistor connected between a third transmission line and the first node connected to a fifth pad of the signal processing unit; and a second resistor connected between the first transmission line and the first node.

15. The ECG patch of claim 14, wherein the first bias voltage and the second bias voltage have a same level.

16. The ECG patch of claim 14, wherein the first ECG signal is detected when the first bias voltage is applied to a person's body, and the second ECU signal is detected when the second bias voltage is applied to the person's body.

17. The ECG patch of claim 14, wherein the high-pass filter is a floating high-pass filter.

18. The ECG patch of claim 14, wherein the high-pass filter comprises:
a first capacitor connected between the first transmission line and the third transmission line, wherein the first transmission line is connected to a first pad of the signal processing unit;
a second capacitor connected between the first wire and a second transmission line, wherein the second capacitor is connected to a second pad of the signal processing unit;
a third resistor connected between the first node and the second transmission line; and
a fourth resistor connected between the first node and the first wire.

19. The ECG patch of claim 18, wherein the first and second capacitors have the same capacitances as each other and the first to fourth resistors have the same resistances as each other.

20. The ECG patch of claim 18, wherein the signal processing unit comprises:
a voltage regulator connected to a third pad of the signal processing unit and configured to receive an operating voltage via the third pad and regulate the operating voltage, wherein the third pad is connected to a second wire;
a voltage divider configured to divide a voltage that has been regulated by the voltage generator to generate a driving voltage; and
a driver configured to drive the driving voltage and provide the driving voltage to the high-pass filter through the fifth pad.

* * * * *